(12) United States Patent
Van Haaften

(10) Patent No.: US 9,238,022 B2
(45) Date of Patent: Jan. 19, 2016

(54) XANTHANODIEN FOR THE TREATMENT OF CANCER

(75) Inventor: Caroline Van Haaften, Leiden (NL)

(73) Assignee: Caroline Van Haaften (NL)

( * ) Notice: Subject to any disclaimer, the term of this patent is extended or adjusted under 35 U.S.C. 154(b) by 0 days.

(21) Appl. No.: 13/261,555

(22) PCT Filed: Jul. 6, 2011

(86) PCT No.: PCT/NL2011/050487
§ 371 (c)(1),
(2), (4) Date: Dec. 31, 2012

(87) PCT Pub. No.: WO2012/005581
PCT Pub. Date: Jan. 12, 2012

(65) Prior Publication Data
US 2013/0123352 A1    May 16, 2013

(30) Foreign Application Priority Data
Jul. 7, 2010  (NL) ...................................... 2005052

(51) Int. Cl.
*A61K 31/343* (2006.01)
*C07D 307/92* (2006.01)
*A61K 31/365* (2006.01)
*A61K 36/28* (2006.01)
*A61K 45/06* (2006.01)

(52) U.S. Cl.
CPC ............. *A61K 31/365* (2013.01); *A61K 31/343* (2013.01); *A61K 36/28* (2013.01); *A61K 45/06* (2013.01)

(58) Field of Classification Search
CPC ............................ A61K 31/343; C07D 307/92
USPC .................. 549/429, 458; 514/449, 461, 468
See application file for complete search history.

(56) References Cited

FOREIGN PATENT DOCUMENTS

WO    WO 2006/067603    6/2006

*Primary Examiner* — Golam M M Shameem
(74) *Attorney, Agent, or Firm* — Banner & Witcoff, Ltd.

(57) ABSTRACT

The present invention relates to a method for the treatment or prophylaxis of a disease associated with hyperproliferative cellular division, comprising administering to a subject in need thereof a therapeutically effective dosage of the pharmaceutical composition comprising xanthanodien, or a pharmaceutically acceptable salt thereof, and a pharmaceutically acceptable carrier.

7 Claims, 8 Drawing Sheets

EPD

EPA

… (US 9,238,022 B2)

XANTHANODIEN FOR THE TREATMENT OF CANCER

TECHNICAL FIELD

The present invention relates to the treatment of diseases associated with hyperproliferative cellular division. In particular, the present invention relates to compounds and compositions for the treatment of diseases associated with hyperproliferative cellular division, in particular cancer, especially ovarian cancer. The inventions further relates to pharmaceutical compositions comprising novel anticancer agents, to methods for the treatment or prophylaxis of a disease associated with hyperproliferative cellular division and to methods for inhibiting the proliferation of cells.

BACKGROUND OF THE INVENTION

Despite intensive research and development into anti-cancer therapies cancer continues to take a heavy toll of lives. More than 10 million people around the world are diagnosed with cancer every year and it is estimated that this number could increase to as many as 20 million new cases a year by 2030. Lung cancer and breast cancer rates in women in particular have risen in recent times and ovarian cancer remains the leading cause of death in women with gynaecological malignancy.

Ovarian cancer is the fifth leading cause of death in women with cancer and remains the leading cause of death from gynaecological malignancy in many countries, in spite of chemotherapy with platinum derivates and/or taxol after surgery. Of the malignant epithelial tumors (>90% of all ovarian cancers), the serous papillary variants form the largest subgroup. Due to its dismal prognosis there is an urgent need for new treatment strategy for ovarian cancer.

Against this background there remains a need for new methods of cancer treatment.

SUMMARY OF THE INVENTION

The present inventor has discovered that a compound isolated from *Calomeria amaranthoides* exhibits very potent anti cancer properties useful in treatment of cancer, and in particular ovarian cancer.

The present inventor discovered that eremophila-1(10)-11(13)-dien-12,8β-olide (EPD) selectively kills cancer cells over normal cells. This is an enormous advantage because standard chemotherapeutics for anti/cancer treatment, such as cisplatin and docetaxol both completely kill cancer cells and normal cells.

In a first aspect, the present invention provides xanthanodien, or a pharmaceutically acceptable salt thereof, for use as a medicament.

In a second aspect, the present invention provides xanthanodien, or a pharmaceutically acceptable salt thereof, for use in the treatment of cancer, preferably ovarian cancer.

In a third aspect, the present invention provides a pharmaceutical composition comprising xanthanodien, or a pharmaceutically acceptable salt thereof, and a pharmaceutically acceptable carrier.

In a preferred embodiment of said aspect, said xanthanodien, or said pharmaceutically acceptable salt thereof, is present in a concentration of greater than 0.001% to less than 20%.

In another preferred embodiment of said aspect, said carrier is selected from the group consisting of aqueous, non-aqueous and nanoparticulate suspensions, solutions, creams, ointments, gels, syrups, suppositories and micro-droplet sprays.

In yet another preferred embodiment of said aspect, said carrier includes an adjuvant selected from the group consisting of builders, stabilizers, emulsifiers, dispersants, preservatives, buffers, electrolytes, tissue penetrating agents and tissue softening agents.

In still another preferred embodiment of said aspect, said composition further comprises at least one chemotherapeutic or other anti-cancer agent.

In a fourth aspect, the present invention provides a method for the treatment or prophylaxis of a disease associated with hyperproliferative cellular division, comprising administering to a subject in need thereof a therapeutically effective dosage of the pharmaceutical composition of the present invention.

In a preferred embodiment of said aspect, said disease associated with hyperproliferative cellular division is cancer, preferably ovarian cancer.

In another preferred embodiment of said aspect, said therapeutically effective dosage is about 0.0001 mg to about 1000 mg per kg body weight of said subject per 24 hours.

In a fifth aspect, the present invention provides the use of xanthanodien, or a pharmaceutically acceptable salt thereof, for the manufacture of a medicament for the treatment or prophylaxis of a disease associated with hyperproliferative cellular division.

In a preferred embodiment of said aspect, said disease associated with hyperproliferative cellular division is cancer, preferably ovarian cancer.

In a sixth aspect, the present invention provides a method for inhibiting the proliferation of cells, said method comprising contacting the cells with a cytotoxic amount of xanthanodien, or a pharmaceutically acceptable salt thereof.

The cells in aspects of the invention are preferably cancer cells or any other cell exhibiting hyperproliferation, in particular ovarian cancer cells.

In a preferred embodiment of said aspect, said cytotoxic amount is in the range of 0.01-100 μg/ml.

The subject in aspects of the present invention is preferably a human, most preferably a female.

DETAILED DESCRIPTION OF THE INVENTION

Definitions

Figure 1:
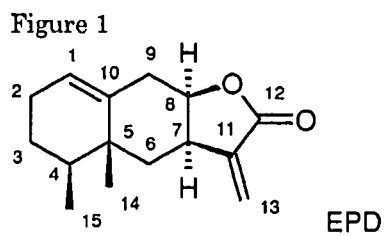
FIG. 1 shows EPD, an α-methylene sesquiterpene lactone.
Figure 2:
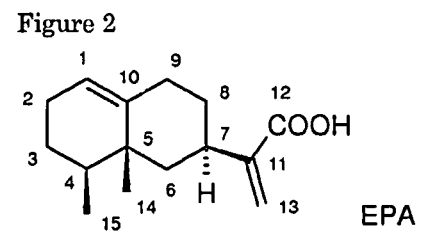
FIG. 2 shows EPA, an α-methylene carboxylic acid.

In the context of this specification, the term "xanthanodien" includes reference to the chemical eremophila-1(10)-11(13)-dien-12,8β-olide (EPD) or (3aα,4aα,5α,9aα)-3a,4,4a,5,6,7,9,9a-octahydro-4a,5-dimethyl-3-methylenenaphtho[2,3-b]furan-2(3H)-2-one, and pharmaceutically acceptable salts thereof. EPD ($C_{15}H_{20}O_2$) is a colourless syrup under standard conditions. EPD has the structural formula:

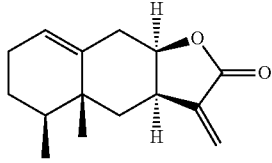

eremophil-1(10), 11(13)-dien-12, 8β-olid (xanthanodien)

$C_{15}H_{20}O_2$ colourless syrup

Structure V, page 1420 in reference:

N Tanaka, T Yazawa, K Aoyama and T Murakami (1976). Chemische Untersuchungen der Inhaltsstoffe von *Xanthium canadense* Mill. Chem. Pharm. Bull. 24(6), 1419-1421.

Proton NMR reveals the following spectrum:
$^1$H-NMR (CDCl$_3$): δ0.92 (s, H-14), 0.93 (d, $J_{4,15}$=6.8 Hz, H-15), 1.50 (m, H-3), 1.60 (m, H-4), 1.70 (m, H-6), 2.03 (m, H-2), 2.30 (m, H-9), 2.58 (dd, $J_{9,9'}$=12.6 Hz, $J_{8,9'}$=7.7 Hz, H-9), 2.92 (m, H-7), 4.53 (dt, $J_{7,8}$=9.6 Hz, $J_{8,9}$=7.4 Hz, H-8), 5.48 (br t, $J_{1,2}$=3.4 Hz, H-1), 5.59 (d, $J_{13,13'}$=2.2 Hz, H-13'), 6.23 (d, $J_{13,13'}$=2.2 Hz, H-13); $^{13}$C-NMR (CDCl$_3$): δ16.08, 20.59, 25.03, 26.72, 34.69, 34.91, 36.63, 37.01, 38.73, 79.00, 121.82, 124.57, 138.32, 139.36, 170.65. Positive ion ESI-MS [M+Na]$^+$ 255 (100), [M+H]+ 233 (65). The term EPD includes reference to chemical derivatives of EPD that exhibit the anti-cancer activity essentially as described herein for EPD.

In the context of this specification, the term "EPA" includes reference to the chemical eremophila-1(10),11(13)-dien-12-oic acid. EPA ($C_{15}H_{22}O_2$) is a colourless syrup under standard conditions. EPA has the structural formula:

eremophilan-12-oic acid type structure

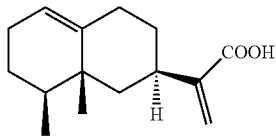

most likely structure

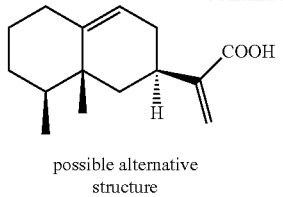

possible alternative structure $C_{15}H_{22}O_2$ colourless syrup

Proton NMR reveals the following spectrum for EPA:
$^1$H-NMR (CDCl$_3$): δ0.85 (d, $J_{4,15}$=6.4 Hz, H-15), 0.91 (s, H-14), 1.45 (m, H-6), 1.50 (m, H-4), 1.55 (m, H-3), 1.60 (m, H-8), 1.85 (m, H-9), 2.01 (m, H-2), 2.40 (m, H-9'), 2.55 (m, H-7), 5.38 (br t, $J_{1,2}$=3.4 Hz, H-1), 5.66 (br s, H-13'), 6.29 (br s, H-13); $^{13}$C-NMR (CDCl$_3$): δ16.08, 20.59, 25.03, 26.72, 34.69, 34.91, 36.63, 37.01, 38.73, 79.00, 121.82, 124.57, 138.32, 139.36, 170.65. Negative ion ESI-MS [M−H]$^-$ 233 (100).

In the context of this specification, a "condition associated with hyperproliferative cellular division" refers to any clinical condition characterised by or otherwise involving an increased rate of cell division relative to a normal reference rate. Conditions associated with hyperproliferative cellular division include, but are not limited to: myeloproliferative syndromes such as Langerhans cell histiocytosis, mastocytosis, mixed myeloproliferative and myelodysplastic conditions, dermal proliferative conditions such as psoriasis, non-bullous congenital ichthyosiform erythroderma. Conditions associated with hyperproliferative cellular division also include cancer, whether benign or malignant, including haematopoietic malignant cancers. In particular, and in preferred embodiments, the term refers to ovarian cancer.

In the context of this specification, the terms "treatment" and "treating" refer to any and all uses which remedy a condition or disease or symptoms thereof, prevent the establishment of a condition or disease or symptoms thereof, or otherwise prevent or hinder or reverse the progression of a condition or disease or other undesirable symptoms in any way whatsoever.

In the context of this specification, the term "therapeutically effective amount" includes within its meaning a non-toxic amount of xanthanodien sufficient to provide the desired therapeutic effect. The exact amount will vary from subject to subject depending on the age of the subject, their general health, the severity of the disorder being treated and the mode of administration. It is therefore not possible to specify an exact "therapeutically effective amount", however one skilled in the art would be capable of determining a "therapeutically effective amount" by routine trial and experimentation.

In the context of this specification, the term "cytotoxic amount" is defined to mean an amount of xanthanodien that is toxic to the target cell once the xanthanodien has associated with the cell. Generally, toxicity is indicated by statistically significant loss in cell viability.

The term "chemotherapeutic agent" refers to a chemical compound useful in the treatment of cancer or other condition characterized by a hyperproliferation of cells.

In the context of this specification, "pharmaceutically acceptable salts" include, but are not limited to, those formed from: acetic, ascorbic, aspartic, benzoic, benzenesulfonic, citric, cinnamic, ethanesulfonic, fumaric, glutamic, glutaric, gluconic, hydrochloric, hydrobromic, lactic, maleic, malic, methanesulfonic, naphthoic, hydroxynaphthoic, naphthalenesulfonic, naphthalenedisulfonic, naphthaleneacrylic, oleic, oxalic, oxaloacetic, phosphoric, pyruvic, p-toluenesulfonic, tartaric, trifluoroacetic, triphenylacetic, tricarballylic, salicylic, sulfuric, sufamic, sulfanilic and succinic acid.

The terms "hyperproliferation" and "hyperproliferating" refer to the abnormal growth of a cell type, which can be cancerous or benign. Generally, hyperproliferating cells exhibit a rate of cell division that is at least about ten percent greater than the rate of cell division exhibited by normal cells of that cell type.

Preferred Embodiments

The anti-cancer activity of *C. amaranthoides* was previously reported by the present inventor in WO 2006/067603. The chemical constituents composition of aerial parts of *C. amaranthoides* have been examined once before by Zdero et al., 1991 Phytochemistry, Vol. 30, No. 8, pp 2643-2650. None of the constituents reported by them were identified in present study of *C. amaranthoides* extracts.

As described herein, the present inventor discovered two very similar sesquiterpenes with the eremophilanolide structure sub-type by $^1$H-NMR and $^{13}$C-NMR and by mass spectrometry in extracts of *C. amaranthoides*. Subsequent comparison with published $^1$H-NMR partial spectra identified the compounds as eremophila-1(10)-11(13)-dien-12,8β-olide (EPD) and eremophila-1(10),11(13)-dien-12-oic acid (EPA). EPD was first discovered in and isolated from the root of *Xanthium canadense* Mill (Tanaka et al., 1976 Chem. Pharm. Bull. 24(6): 1419-1421). EPA was first isolated from *Inula* species (Bohlmann et al. 1977. Phytochemistry 16: 1302-1303).

Surprisingly, only one of these compounds exhibited the cytotoxic effects as observed for the *C. amaranthoides* extract. While EPA did not show cytotoxic effects, EPD was found to have very potent anti-cancer properties. The cytotoxic effects of the crude extracts of *C. amaranthoides* are clearly indicated at concentrations of for instance 10 μg/mL using in vitro test conditions. Similarly, the isolated biologically active compound EPD has been shown to kill completely ovarian cancer cells under in vitro conditions at concentrations below 10 μg/mL, such as 5 μg/mL. In addition, substantial killing of cancer cells is already observed at concentrations as low as of 1 μg/mL.

Interestingly, and similar to the crude plant extract, EPD selectively kills cancer cells. This is an enormous advantage because standard chemotherapeutics for anti/cancer treatment, such as cisplatin and docetaxol both completely kill cancer cells and normal cells in parallel experiments conducted by the inventor.

In one aspect, the present invention relates to a method for inhibiting the proliferation of cells comprising contacting the cells with xanthanodien. The skilled person will understand that also a prodrug thereof, may be administered. In the context of this specification, the term "prodrug" refers to a pharmacologically inactive compound that converts to the active compound within the human body.

Xanthanodien may be extracted from selected plants, for example *Calomeria amaranthiodes* aka: *Humea elegans*. Alternatively, xanthanodien may be prepared from known starting materials according to literature procedures. See for example Zoretic et al., *J. Org. Chem.* (1982), 47, 1327, Tada et al. *J. Chem. Soc. Perkin Trans.* 1 (1993), 239 and WO2006/067603.

Also of great interest is that the compound discovered as the active anti-cancer substance in extracts of the *C. amaranthoides* can surprisingly easy be extracted from (parts of) the plant using steam distillation procedures. Steam distillation is a process whereby a mixture of two practically immiscible liquids are heated while being agitated to expose the surfaces of both the liquids to the vapor phase, each constituent independently exerting its own vapor pressure as a function of temperature as if the other constituent were not present. Consequently, the vapor pressure of the whole system increases. Boiling begins when the sum of the partial pressures of the two immiscible liquids just exceeds the atmospheric pressure (approximately 101 kPa at sea level). In this way, many organic compounds insoluble in water can be purified at a temperature well below the point at which decomposition occurs. In the present case, EPD has now been shown to be readily distilled at a temperature well below its normal boiling point. This technique is very advantageous over for instance chromatographic techniques for purification, or conventional distillation.

Hence, in another aspect, the present invention provides a method for purifying the anti-cancer compound EPD from plant parts of *C. amaranthoides*, said method comprising subjecting said plant parts to steam distillation.

Purification of EPD from *C. amaranthoides* can be done as follows. The typical *C. amaranthoides* harvest begins when the *C. amaranthoides* plant reaches a certain maturity, which is ideally when the plant contains the most EPD, and has desired qualities. When the majority of the plants reach this stage, the plants are cut or mowed. Typically the *C. amaranthoides* will be cut or harvested using a machine such as a windrower. Small plots may be cut by hand. The *C. amaranthoides* plants are cut at ground level. Alternatively, the leaves may be removed from the stems and harvested separately. The harvested *C. amaranthoides* material is preferably allowed to air dry for a period of time to reach a desired moisture-content for distillation. Typically to prepare cuttings or leaves for chopping, cuttings or leaves would be dried to a moisture-content, of approximately 40% based on the fresh weight of the plants at harvest. When the cuttings or leaves are dried to the desired moisture-content the plant material is then chopped or cut to a desired length, typically about 0.1-2 inches, and the chopped plant parts collected in a vessel through which steam can be led. The steam distillation is accomplished by leading (preferably pressurized) steam through the chopped plant parts. As the steam filters through the chopped plant material, the EPD is vaporized and extracted from the *C. amaranthoides* plant material with the steam and is carried together with the steam to a condensation and separation apparatus. Hence, preferably, the steam, after passing through chopped plant parts, is collected and then routed to a condensation and separation apparatus. The condensation apparatus may be a condenser where steam and EPD are condensed and pure EPD is collected from the condenser into, for instance, a separating vessel by using a separator. After purification, the pure EPD may be crystallized to reach even higher purities.

The invention further relates to a method for the treatment or prophylaxis of a condition associated with hyperproliferative cellular division in a subject in need thereof comprising administration to the subject of a therapeutically effective amount of xanthanodien, as defined above. The condition associated with hyperproliferative cellular division may be cancer.

The cancer may be selected from the group consisting of: gastrointestinal tumours, cancer of the liver and biliary tract, pancreatic cancer, prostate cancer, testicular cancer, blood cancer, lung cancer, skin cancer (for example melanoma), breast cancer, non-melanoma skin cancer (for example basal cell carcinoma and squamous cell carcinoma), ovarian cancer, uterine cancer, cervical cancer, cancer of the head and neck, bladder cancer, sarcomas and osteosarcomas, Kaposi sarcoma, AIDS-related Kaposi sarcoma and renal carcinoma. In one embodiment, the cancer is ovarian cancer.

Xanthanodien is useful as therapeutic agent in the treatment or prevention of conditions associated with hyperproliferative cellular division, such as cancer. Xanthanodien may suitably be administered to a subject (for example a human) in the form of pharmaceutical compositions.

Pharmaceutical compositions include those suitable for oral, parenteral (including subcutaneous, intradermal, intramuscular, intravenous and intraarticular), inhalation (including use of metered dose pressurised aerosols, nebulisers or insufflators), rectal and topical (including dermal, buccal, sublingual and intraocular) administration.

The compositions may conveniently be presented in unit dosage form and may be prepared by any of the methods well known in the art of pharmacy. All methods include the step of bringing xanthanodien as defined herein into association with a carrier which constitutes one or more accessory ingredients. In general, the compositions are prepared by uniformly and intimately bringing into association the xanthanodien with a liquid carrier or finely divided solid carrier, or both and then, if necessary, shaping the product into the desired composition.

Generally, an effective dosage of xanthanodien present in pharmaceutical and other compositions of the present invention is expected to be in the range of about 0.0001 mg to about 1000 mg per kg body weight per 24 hours; about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours, or about 1.0 mg to about 250 mg per kg body weight per 24 hours. More typically, an effective dose range is expected to be in the range of about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours, or about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, about 25 to about 350 mg/m$^2$, about 25 to about 300 mg/m$^2$, about 25 to about 250 mg/m$^2$, about 50 to about 250 mg/m$^2$, or about 75 to about 150 mg/m$^2$.

Compositions suitable for buccal (sublingual) administration include lozenges comprising xanthanodien in a flavoured base, usually sucrose and acacia or tragacanth; and pastilles comprising xanthanodien in an inert base such as gelatine and glycerin or sucrose and acacia.

Compositions comprising xanthanodien suitable for oral administration may be presented as discrete units such as gelatine or HPMC capsules, cachets or tablets, each containing a predetermined amount of xanthanodien, as a powder, granules, as a solution or a suspension in an aqueous liquid or a non-aqueous liquid, or as an oil-in-water liquid emulsion or a water-in-oil liquid emulsion. Xanthanodien may also be present in a paste.

When the compositions comprising xanthanodien are formulated as capsules, the xanthanodien may be formulated with one or more pharmaceutically acceptable carriers such as starch, lactose, microcrystalline cellulose, silicon dioxide and/or a cyclic oligosaccharide such as cyclodextrin. Additional ingredients may include lubricants such as magnesium stearate and/or calcium stearate. Suitable cyclodextrins include α-cyclodextrin, β-cyclodextrin, γ-cyclodextrin, 2-hydroxyethyl-β-cyclodextrin, 2-hydroxypropyl-cyclodextrin, 3-hydroxypropyl-β-cyclodextrin and tri-methyl-β-cyclodextrin. The cyclodextrin may be hydroxypropyl-β-cyclodextrin. Suitable derivatives of cyclodextrins include Captisol® a sulfobutyl ether derivative of cyclodextrin and analogues thereof as described in U.S. Pat. No. 5,134,127.

Tablets may be prepared by compression or moulding, optionally with one or more accessory ingredients. Compressed tablets may be prepared by compressing in a suitable machine xanthanodien in a free-flowing form such as a powder or granules, optionally mixed with a binder, lubricant (for example magnesium stearate or calcium stearate), inert diluent or a surface active/dispersing agent. Moulded tablets may be made by moulding a mixture of the powdered xanthanodien moistened with an inert liquid diluent, in a suitable machine. The tablets may optionally be coated, for example, with an enteric coating and may be formulated so as to provide slow or controlled release of xanthanodien therein.

Compositions for parenteral administration include aqueous and non-aqueous sterile injectable solutions which may contain anti-oxidants, buffers, bacteriostats and solutes which render the formulation isotonic with the blood of the intended recipient, and which may include suspending agents and thickening agents. A parenteral composition may comprise a cyclic oligosaccaride such as hydroxypropyl-β-cyclodextrin. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use.

Compositions suitable for transdermal administration may be presented as discrete patches adapted to remain in intimate contact with the epidermis of the recipient for a prolonged period of time. Such patches suitably comprise xanthanodien as an optionally buffered aqueous solution of, for example, 0.1 M to 0.2 M concentration with respect to the compound.

Compositions suitable for transdermal administration may also be delivered by iontophoresis, and typically take the form of an optionally buffered aqueous solution of the active compound. Suitable compositions may comprise citrate or Bis/Tris buffer (pH 6) or ethanol/water and contain from 0.1 M to 0.2 M of xanthanodien.

Spray compositions for topical delivery to the lung by inhalation may, for example be formulated as aqueous solutions or suspensions or as aerosols, suspensions or solutions delivered from pressurised packs, such as a metered dose inhaler, with the use of a suitable liquefied propellant. Suitable propellants include a fluorocarbon or a hydrogen-containing chlorofluorocarbon or mixtures thereof, particularly hydrofluoroalkanes, e.g. dichlorodifluoromethane, trichlorofluoromethane, dichlorotetrafluoroethane, especially 1,1,1,2-tetrafluoroethane, 1,1,2,2,3,3,3-heptafluoro-n-propane or a mixture thereof. Carbon dioxide or other suitable gas may also be used as propellant. The aerosol composition may be excipient free or may optionally contain additional composition excipients well known in the art, such as surfactants e.g. oleic acid or lecithin and cosolvents e.g. ethanol. Pressurised compositions will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. When the excipient is lactose it will typically be present as milled lactose, wherein not more than 85% of lactose particles will have a MMD of 60-90 μm and not less than 15% will have a MMD of less than 15 μm.

Compositions for rectal administration may be presented as a suppository with carriers such as cocoa butter or polyethylene glycol, or as an enema wherein the carrier is an isotonic liquid such as saline. Additional components of the compositions may include a cyclic oligosaccaride, for example, a cyclodextrin, as described above, such as hydroxypropyl-β-cyclodextrin, one or more surfactants, buffer salts or acid or alkali to adjust the pH, isotonicity adjusting agents and/or anti-oxidants.

Compositions suitable for topical administration to the skin preferably take the form of an ointment, cream, lotion, paste, gel, spray, aerosol, or oil. Carriers which may be used include Vasoline, lanoline, polyethylene glycols, alcohols, and combination of two or more thereof. Xanthanodien is generally present at a concentration of from 0.1% to 20% w/w, or from 0.5% to 5% w/w. Examples of such compositions include cosmetic skin creams.

The composition may also be administered or delivered to target cells in the form of liposomes. Liposomes are generally derived from phospholipids or other lipid substances and are formed by mono- or multi-lamellar hydrated liquid crystals that are dispersed in an aqueous medium. Specific examples of liposomes that may be used to administer or deliver a compound formula (I) include synthetic cholesterol, 1,2-distearoyl-sn-glycero-3-phosphocholine, 3-N-[(-methoxy poly (ethylene glycol)2000)carbamoyl]-1,2-dimyrestyloxy-propylamine (PEG-CDMA) and 1,2-di-o-octadecenyl-3-(N,N-dimethyl)aminopropane (DODMA).

The compositions may also be administered in the form of microparticles. Biodegradable microparticles formed from polylactide (PLA), polylactide-co-glycolide (PLGA), and ε-caprolactone have been extensively used as drug carriers to increase plasma half life and thereby prolong efficacy (R. Kumar, M., 2000, *J Pharm Pharmaceut Sci*. 3(2) 234-258).

The compositions may incorporate a controlled release matrix that is composed of sucrose acetate isobutyrate (SAIB) and organic solvent or organic solvent mixtures. Polymer additives may be added to the vehicle as a release modifier to further increase the viscosity and slow down the release rate. Xanthanodien may be added to the SAIB delivery vehicle to form SAIB solution or suspension compositions. When the formulation is injected subcutaneously, the solvent diffuses from the matrix allowing the SAIB-drug or SAIB-drug-polymer mixtures to set up as an in situ forming depot.

In the treatment of cancer, therapeutic advantages may be obtained through combination treatment regimens. As such, methods of treatment according to the present invention may be used in conjunction with other therapies, such as radiotherapy, chemotherapy, surgery, or other forms of medical intervention. Non-limiting examples of suitable chemotherapeutic and other anti-cancer agents include: taxol, fluorouracil, cisplatin, oxaliplatin, α-interferon, vincristine, vinblastine, angioinhibins, doxorubicin, bleomycin, mitomycin C, phenoxodiol, methramycin, TNP-470, pentosan polysulfate, tamoxifen, LM-609, CM-101 and SU-101.

The co-administration of xanthanodien and chemotherapeutic or other anti-cancer agents may be simultaneous or sequential. Simultaneous administration may be effected by xanthanodien being in the same unit dose as a chemotherapeutic or other anti-cancer agent, or xanthanodien and the chemotherapeutic or other anti-cancer agents may be present in individual and discrete unit doses administered at the same, or at a similar time. Sequential administration may be in any order as required.

All publications mentioned in this specification are herein incorporated by reference. The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be further described in greater detail by reference to the following specific examples, which should not be construed as in any way limiting the scope of the invention.

EXAMPLES

Example 1

Isolation of Compounds from *Calomeria amaranthoides* and Cell Viability Tests

Materials and Methods
Plant Material

Leaves of *C. amaranthoides*, gathered in the Blue Mountains (NSW, Australia) and confirmed by the Mount Tomah Botanic Garden (NSW, Australia) were air-dried protected from sunlight.
Cell Lines and Cell Cultures Cells used in the assays were an ovarian cell line, JC (van Haaften-Day et al. 1983. Cancer Research 43: 3725-3731), OVCAR-3 and SKOV-3, The American Type Culture Collection (ATCC), a melanoma line (MM-An, Byers et al. 1991. Am J Path 139, No 2: 423-435) and normal human diploid fibroblasts primary cultures (Brookes et al. 2002 The EMBO Journal Vol. 21, No. 12: 2936-2945).
In Vitro Cytotoxicity Tests with a Compound, Isolated from the Leaves of *C. amaranthoides*

In vitro cytotoxicity tests were performed using a non-fluorescent substrate, Alamar blue (BioSource, Invitrogen, UK) as described by Page et al. (Page B, Page M and Noel C. 1993. International Journal of Oncology 3: 473-476).

Ovarian cancer cells ($1\times10^4$ or $5\times10^4$) were seeded in 24-well plates (Costar, USA) and grown in RPMI-1640, supplemented with 6 mM L-glutamine, 10% fetal calf serum (FCS) (Gibco, Invitrogen, UK) and penicillin (100 units/mL) and streptomycin (100 μg/mL), while melanoma cells and normal fibroblasts were grown in Dulbecco's modified Eagle medium (DMEM), also supplemented with L-glutamine and FCS. The cultures were maintained in a humidified atmosphere of 5% $CO_2$ at 37° C.

The in exponential growth cultures (in triplicates) were treated with the compound, dissolved in dimethyl sulfoxide (DMSO) and added at final concentrations of 1, 5, and 10 μg/mL. In 2 mL medium/well 10% Alamar blue was added and 100 μl of the supernatant of the 24-well plates after 24, 48 and 72 hrs were pipetted into 96-well plates (Costar, USA). Cell viability was measured with a 96-well plate reader (Molecular Devices Ltd, UK).
$^1$H-NMR and $^{13}$C-NMR Analyses $^1$H-NMR and $^{13}$C-NMR spectroscopy was performed on those plant fractions with clear cytotoxicity effects. $^1$H-NMR, $^{13}$C-NMR and Correlation Spectroscopy (COSY) spectrum was performed using a Varian Gemini 300 MHz instrument (Palo Alto, Calif., USA). The spectra were measured in parts per million (ppm) and were referenced to tetramethylsilane (TMS=0 ppm).

Electrospray ionisation in negative mode (ESI) mass spectrometry analyses were performed using a Thermo TSQ 7000 Liquid Chromatography Mass Spectrometer (LC-MS/MS) (San Jose, Calif., USA) equipped with Xcalibur data acquisition and processing software.

Short-Column Vacuum Chromatography (SCVC) was performed using a column packed with TLC-grade silica gel H60 (Merck, Darmstadt, Germany)) and applying a step-wise gradient of solvents with increasing polarity. Substances were detected by TLC performed on silica gel coated TLC plates (H60 F254, Merck), by molecular weight (ESI-MS) and by $^1$H-NMR spectroscopy.

Results

Fractionation of Extracts by Column Chromatography:

Dried plant material (approx. 350 g), cut in small pieces was soaked in chloroform at room temperature. After 24-48 hrs the crude extract of the leaves was evaporated under reduced pressure and the residue, redissolved in 30 mL applied to a column (21 cm×5 cm i.d.) filled with Silicagel (Lichroprep Si 60, particle size 15-25 μm) Merck). Elution was carried out with a stepwise solvent gradient made up of combinations of hexane, chloroform, dioxane, ethyl acetate, 2-butanone, acetone, 2-propanol and methanol (Table I). The fraction eluting in hexane:chloroform:dioxane:ethyl acetate: 2-propanol, 80:10:2:6:1 (v/v, 600 mL) was selected for high resolution fractionation.

TABLE 1

| Fractions | ml  | H  | C  | DO | EA | EMK | A  | 2P | M  |
|-----------|-----|----|----|----|----|-----|----|----|----|
| 1-11      | 200 | 99 |    | 1  |    |     |    |    |    |
| 11-22     | 200 | 98 |    | 2  |    |     |    |    |    |
| 22-33     | 200 | 88 | 10 | 2  |    |     |    |    |    |
| 33-55     | 400 | 68 | 20 | 2  |    |     |    |    |    |
| 53-86     | 600 | 80 | 10 | 2  | 6  |     | 1  |    |    |
| 86-97     | 200 | 88 | 10 | 2  | 12 | 4   | 2  |    | 2  |
| 97-108    | 200 | 56 | 20 |    |    |     | 16 | 8  |    |
| 108-119   | 200 | 36 | 40 |    |    |     | 8  |    | 16 |
| 119-130   | 200 | 36 | 40 |    |    |     | 16 |    | 8  |
| 130-141   | 200 |    | 40 |    |    |     | 20 |    | 40 |
| 141-152   | 200 |    | 20 |    |    |     | 40 |    | 40 |
| 152-157   | 100 |    | 50 |    |    |     |    |    | 50 |

H = hexane, C = chloroform, DO = dioxane, EA = ethyl acetate, EMK = ethylmethylketone, A = acetone, 2P = 2-propanol, M = methanol High-Performance Liquid Chromatography (HPLC) Fractionation:

Further fractionation was carried out by HPLC using the Akta purifier (Amersham Pharmacia Biotech, Sweden) using a HPLC-column (150 mm×4.6 mm i.d. plus pre-column; Grace-Alltech, The Netherlands), filled with HS Silica (particle size 3 μm). Ten μL of the fraction were injected after dilution to 100 μL with eluent A: hexane (99.5 mL)-dioxane (0.5 mL). The first 10 minutes the column was eluted at a flow rate of 0.5 mL/min with eluent A: hexane (99.5 mL)-dioxane (0.5 mL), followed by 30 minutes with eluent B: hexane (85 mL)-diethyl ether (10 mL)-ethanol (5 mL).

Four groups of fractions (fractions: 1-6, 60-70, 90-100 and 120-130) were collected and assayed for cytotoxicity towards ovarian cancer cells. Group 2 (fraction 60-70) showed the strongest cytotoxicity, killing all cells at 5-10 μg/mL but not at 1 μg/mL. Other fractions did not show significant activity.

The second group of fractions (60-70) was further fractionated by normal-phase short-column vacuum chromatography on silica gel H (Column dimensions 18 mm×65 mm id.), eluted with stepwise solvent gradients of hexane:dichloromethane, 1:1 v/v (100 mL and 50 mL); dichloromethane (2×50 mL); dichloromethane:ethyl acetate, 4:1 v/v (2×50 mL); dichloromethane:ethyl acetate, 1:1 v/v (2×50 mL); ethyl acetate (2×50 mL). From each fraction (12 in total) solvents were evaporated under reduced pressure and the residue was weighed.

Bioassay with ovarian cancer cells indicated Fraction 4 (309 mg) (out of the twelve fractions, see above) as the fraction with most of the cytotoxicity and its main chemical constituent was identified as EPD (see Formula above) by $^1$H-NMR analysis at 56% purity. A second main non-cytotoxic constituent present mostly in Fractions 7 to 9 was identified as EPA (137 mg, 91% purity by NMR and MS analyses).

Again fractionation was applied to Fraction 4 enriched in EPD using normal-phase short-column vacuum chromatography (Column phase silica gel H; dimensions 18 mm×65 mm i.d.), eluting with a stepwise solvent gradient of hexane: dichloromethane, 2:1 v/v (100 mL); hexane:dichloromethane, 1:1 v/v (2×50 mL); hexane:dichloromethane, 1:2 v/v (2×50 mL); dichloromethane (2×50 mL); dichloromethane:ethyl acetate 4:1 (2×50 mL); dichloromethane: ethyl acetate, 1:1 v/v (2×50 mL) to give the main chemical constituent, identified as a SL, EPD (93 mg, 85% purity by NMR and MS analyses) and containing lipids and waxes (15% by NMR analyses).

$^1$H-NMR and $^{13}$C-NMR Analyses:

Eremophila-1(10)-11(13)-dien-12,8β-olide (EPD) (3aα, 4aα,5α,9aα)-3a,4,4a,5,6,7,9,9a-octahydro-4a, 5-dimethyl-3-methylenenaphtho[2,3-b]furan-2(3H)-2-one $C_{16}H_{20}O_2$ colourless liquid; $^1$H-NMR (CDCl$_3$): 0.92 (s, H-14), 0.93 (d, $J_{4,15}$=6.8 Hz, H-15), 1.50 (m, H-3), 1.60 (m, H-4), 1.70 (m, H-6), 2.03 (m, H-2), 2.30 (m, H-9), 2.58 (dd, $J_{9,9'}$=12.6 Hz, $J_{8,9'}$=7.7 Hz, H-9'), 2.92 (m, H-7), 4.53 (dt, $J_{7,8}$=9.6 Hz, $J_{8,9}$=7.4 Hz, H-8), 5.48 (br t, $J_{1,2}$=3.4 Hz, H-1), 5.59 (d, $J_{13,13'}$=2.2 Hz, H-13'), 6.23 (d, $J_{13,13'}$=2.2 Hz, H-13); $^{13}$C-NMR (CDCl$_3$): 16.08, 20.59, 25.03, 26.72, 34.69, 34.91, 36.63, 37.01, 38.73, 79.00, 121.82, 124.57, 138.32, 139.36, 170.65. Positive ion ESI-MS [M+Na]$^+$ 255 (100), [M+H]+ 233 (65).

Eremophila-1(10),11(13)-dien-12-oic acid (EPA) $C_{15}H_{22}O_2$ colourless liquid; $^1$H-NMR (CDCl$_3$): 0.85 (d, $J_{4,15}$=6.4 Hz, H-15), 0.91 (s, H-14), 1.45 (m, H-6), 1.50 (m, H-4), 1.55 (m, H-3), 1.60 (m, H-8), 1.85 (m, H-9), 2.01 (m, H-2), 2.40 (m, H-9'), 2.55 (m, H-7), 5.38 (br t, $J_{1,2}$=3.4 Hz, H-1), 5.66 (br s, H-13), 6.29 (br s, H-13); $^{13}$C-NMR (CDCl$_3$): 16.08, 20.59, 25.03, 26.72, 34.69, 34.91, 36.63, 37.01, 38.73, 79.00, 121.82, 124.57, 138.32, 139.36, 170.65. Negative ion ESI-MS [M−H]$^−$ 233 (100).

Cell Viability with EPD and EPA

Figure 3:
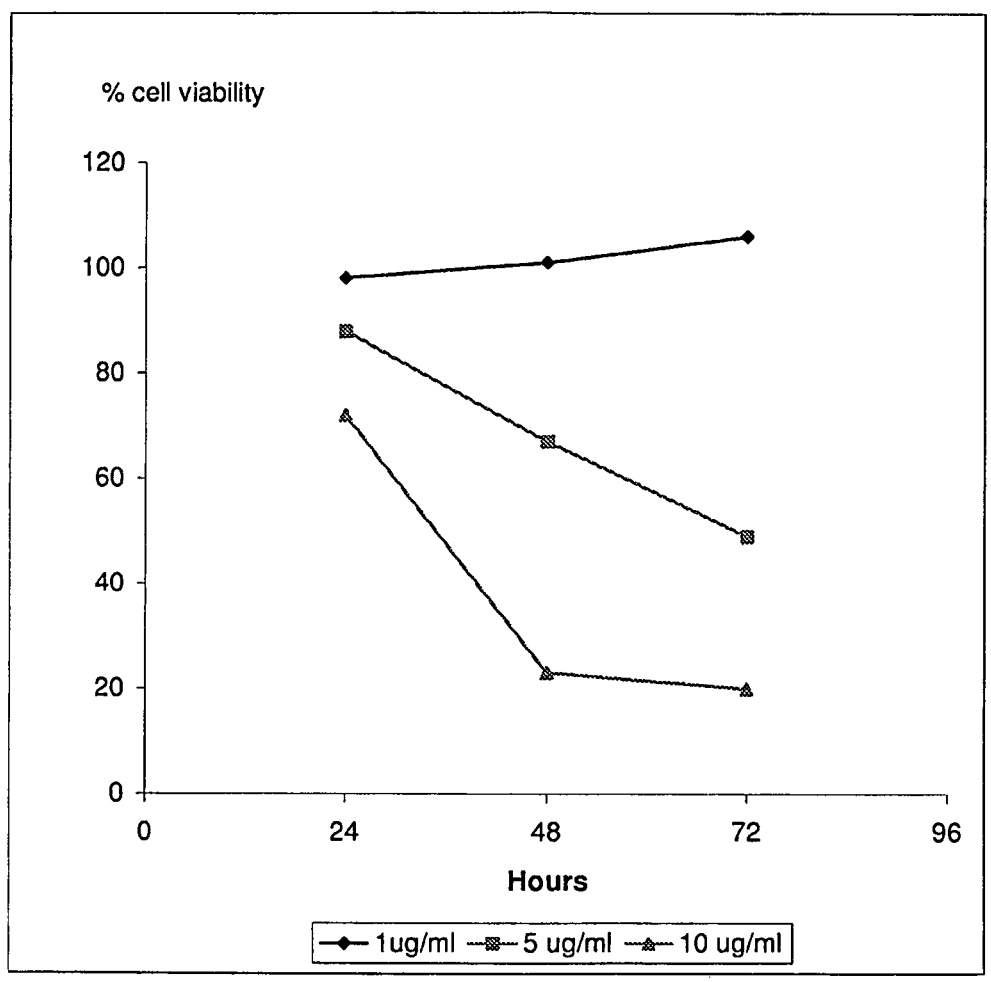
FIG. 3 shows cell viability of an ovarian cancer cell line, (NIH:OVCAR-3) in the presence of EPD at concentrations of 1, 5 and 10 μg/mL at 24, 48 and 72 hours.
Figure 4:
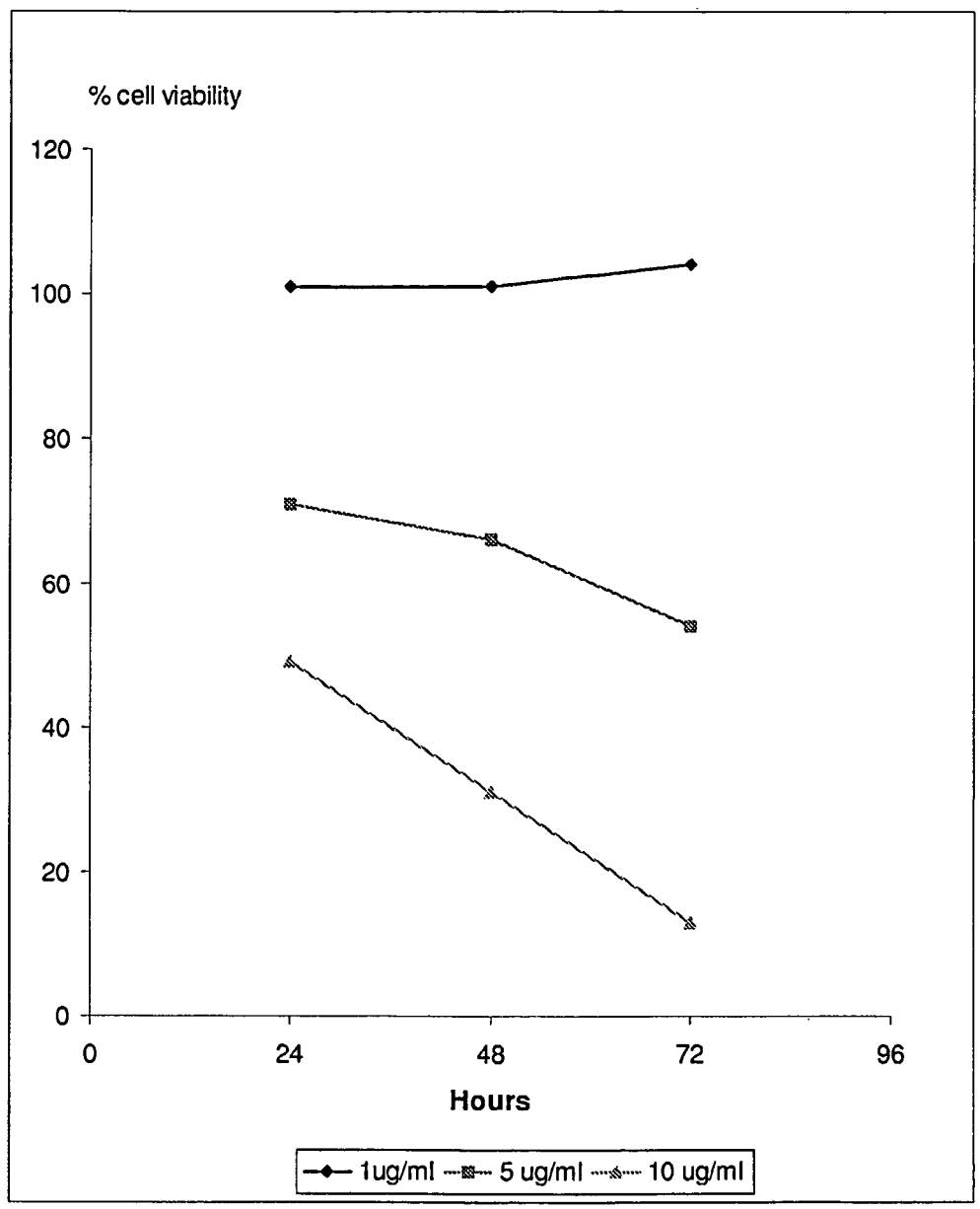
FIG. 4 shows in vitro cell viability of ovarian cancer cells (SKOV-3) in the presence of EPD at concentrations of 1, 5 and 10 μg/mL at 24, 48 and 72 hours.
Figure 5:
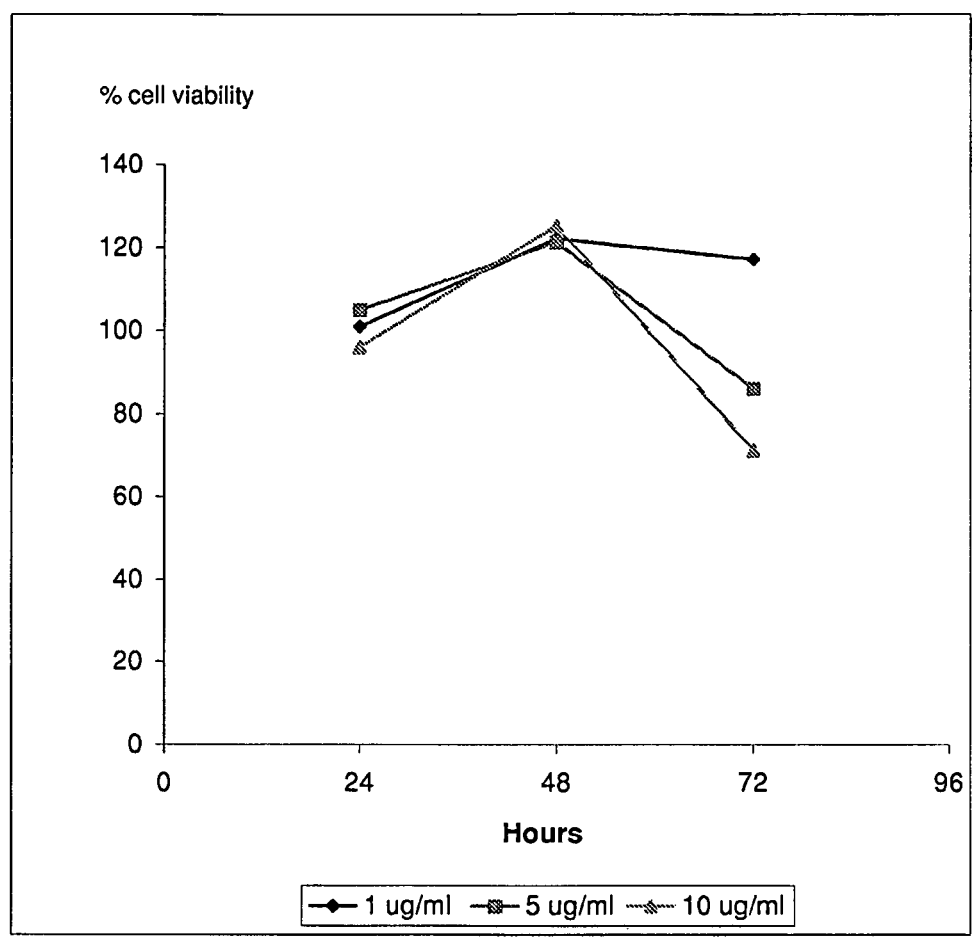
FIG. 5 shows cell viability of normal skin fibroblasts treated with EPD at concentrations of 1, 5 and 10 μg/mL at 24, 48 and 72 hours.

Ovarian cancer cells JC, NIH:OVCAR-3, Skov-3, fibroblasts as well as melanoma cancer cells MM-AN were used for cytotoxicity tests with EPD and EPA. The final concentrations of EPD and EPA added to the growth medium were 1, 5 and 10 μg/ml per well. With the purified compound EPD the cancer cells were killed between 1 and 5 μg/mL and at 1 μg/mL many cancer cells were floating in the wells. Normal cells were not or little affected at 5 μg/mL (FIGS. 3-5).

With the purified compound EPA no cytotoxicity was noted at the concentrations 1, 5 and 10 μg/mL in the cell lines or cell cultures described.

Figure 6:
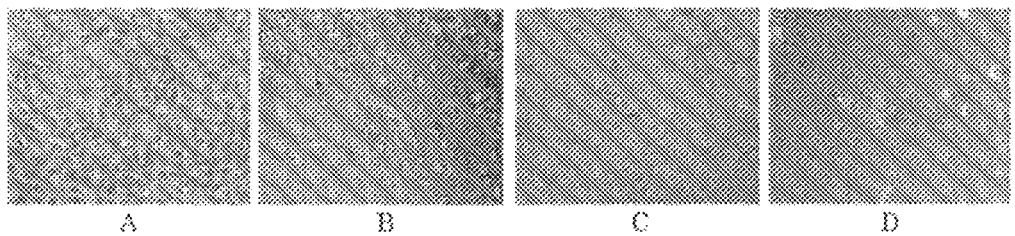
FIG. 6 shows a photograph taken with a camera on an inverted microscope (100×) of ovarian cancer cells, JC, and subsequently shows control (A) treated with 1 (B), 5 (C) and 10 (D) μg/mL of EPD after 48 hours.
Figure 7:
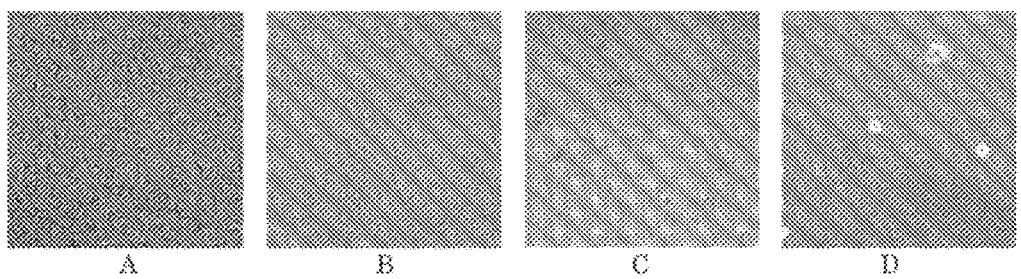
FIG. 7 shows a photograph taken with a camera on an inverted microscope (100×) of melanoma cells, MM-AN, and subsequently shows control (A) treated with 1 (B), 5 (C) and 10 (D) μg/mL of EPD after 48 hours.
Figure 8:
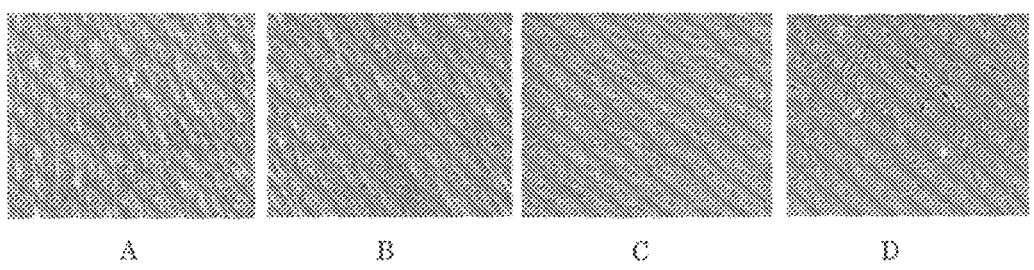
FIG. 8 shows a photograph of human fibroblasts (100×), and subsequently shows control (A) treated with 1 (B), 5 (C) and 10 (D) μg/mL of EPD after 48 hours.
Figure 9:
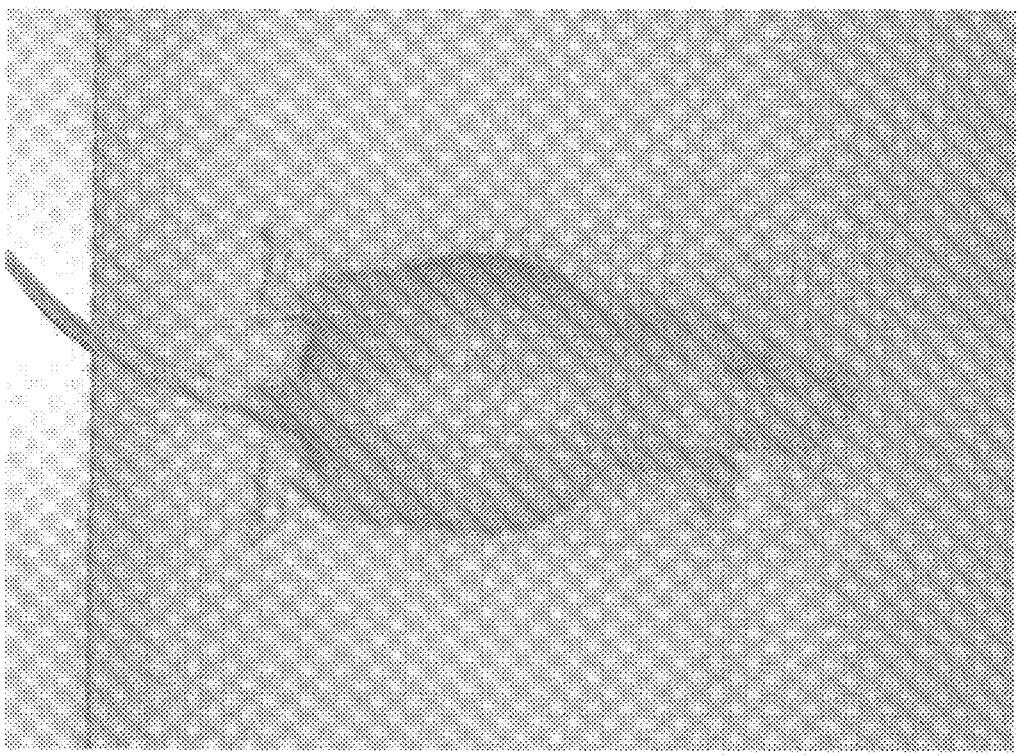
FIG. 9 shows a photograph of a nude mouse inoculated with OVCAR-3 cells and developing ascites as described in Example 2.
Figure 10:
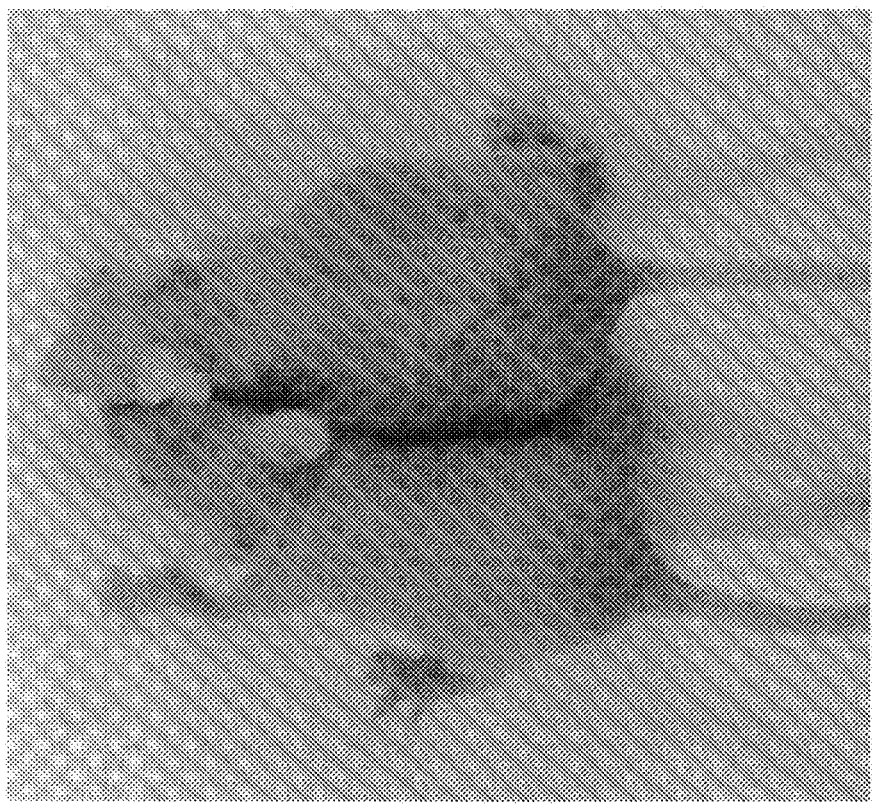
FIG. 10 shows a photograph of two mice inoculated with OVCAR-3 cells, both of which developed ascites, but only one of which was treated with EPD (the lower animal) as described in Example 2. In this treated mouse the ascites disappeared indicating effective treatment with EPD.
Figure 11:
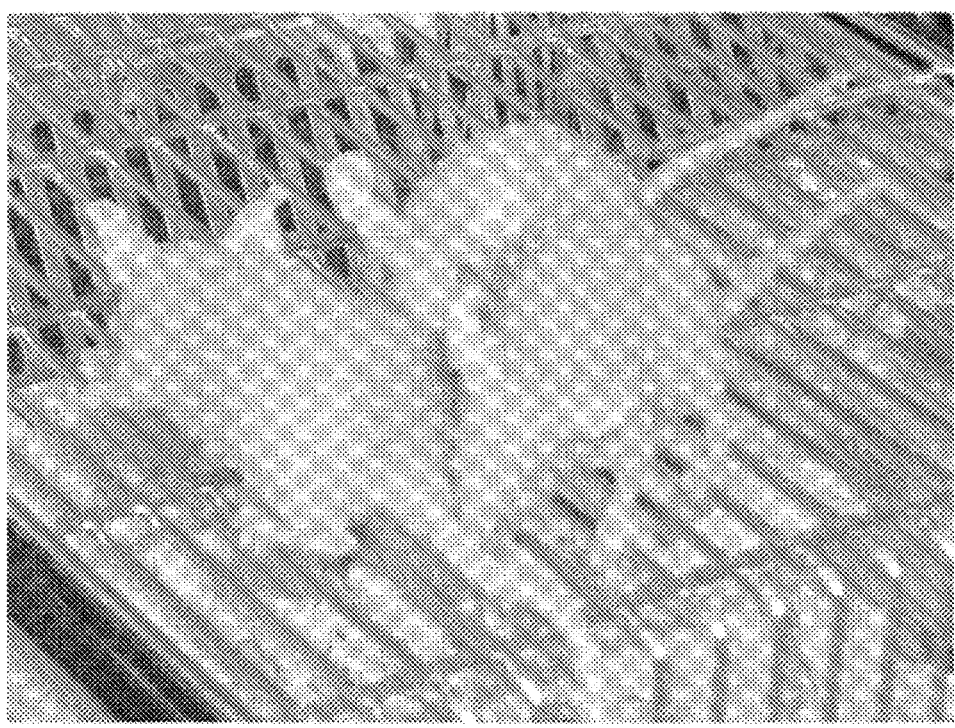
FIG. 11 shows healthy control mice.

Photographs were taken from the ovarian cancer cell line JC, the melanoma cell line MM-An and normal fibroblasts in 24-well plates using a Leica inverted microscope at a magnification of 100 times. Concentrations of EPD ranged 1-10 μg/mL and the experiments were terminated at 48 and 72 hrs (FIGS. 6-8).

It was observed that with increasing concentration of EPD, cell death increased. Cell death was observed in the majority of cancer cells following exposure to 5 µg/mL of EPD for 48 hours. All cells were dead following exposure to 10 µg/mL of EPD for 48 hours. In contrast, the normal fibroblasts appeared largely unaffected following exposure to 5 µg/mL after 48 hours, with more evidence of cell death at 10 µg/mL.

Cell viability was measured by adding 10% Alamar Blue (BioSource, Invitrogen, UK) to ovarian cancer cell cultures (OVCAR-3, SKOV-3) to 1, 5 and 10 µg/ml of EPD and to the control cultures (as described above). After 24, 48 and 72 hours incubation, 100 µl of culture supernatant was taken and cell viability measured with a plate reader (Molecular Devices, Ltd, UK) according to the manufacturer's instructions. The results are depicted in FIGS. 3-5 and confirm that the phenomenon observed in the photographs of FIGS. 6-8 is cell death. It is also noted that EPD showed significant activity against multiple ovarian cancer cell lines.

Example 2

In Vivo Assessment of the Efficacy of EPD in the Treatment of Ovarian Cancer

Ovarian cancer is the major gynaecologic cancer. The cancer often becomes manifest at advanced stages (Stage III, IV), having spread from the ovaries into the peritoneal (abdominal) cavity, where the cancer gives rise to ascites or hydroperitoneum, a pathological accumulation of fluid in the peritoneal cavity.

Ovarian Cancer Animal Model: Granted by the Animal Ethical Committee (DEC), The Netherlands In order to assess the efficacy of EPD in the treatment of ovarian cancer, in vivo experiments were performed with Balb/c nu/nu mice (Charles River Laboratories, France). As a model system of advanced ovarian cancer, a total of 20 Balb/c nu/nu mice were inoculated intra-peritoneally (i.p.) with $1.0 \times 10^7$ cells NIH:OVCAR-3 cells (American Type Culture Collection (ATCC number: HTB-161™)/200 µl PBS. NIH:OVCAR-3 is an appropriate model system in which to study drug resistance in ovarian cancer. Upon inoculation into the abdominal cavity ascites were formed at first in only 5 mice. One mouse after having developed a large abdomen was sacrificed and the ascites cells were inoculated into the 15 mice which had not developed ascites. Another mouse was sacrificed to freeze down the cells. The three other mice were treated with EPD (400 ug/kg) for six weeks, their abdomen was reduced to normal size, and then kept alive for another month to see if they would develop ascites again. The 15 mice without ascites were devided into 3 groups of 5 mice. One group served as control, one group received the standard chemotherapy cisplatin and one group received the test drug EPD.

Treatment Regime

Drugs were given 200 µl/mouse i.p. in order to assess their efficacy as anti-tumor drug. The weight of mice when drug-treated varied between 22 and 26 gram, all with a swollen abdomen. Reduction of the swollen abdomen of the mice (resulting from the killing of the OVCAR-3 cells) was then studied. Cisplatin (Platosin®; Pharma Chemie, The Netherlands) was administered at a dosage of 5 mg/kg body weight i.p. once a week as positive control.

Eremophila-1(10)-11(13)-dien-12,8β-olide (EPD) was administered at 20 mg/kg body weight. EPD was isolated from *Calomeria amaranthoides* as described in Example 1 above. The drug was inoculated twice a week into the abdominal cavity of the mice. EPD was administered for a total period of 6 weeks and cisplatin was administered for a total period of 4 weeks.

Results

In EPD treated mice the swelling of the abodomen was reduced during treatment. Also in cisplatin treated mice the swelling of the abodomen was reduced during treatment. If the swelling was already too advances, neither of the treatments described were effective indicating that the disease was too advanced. This reduction in swelling indicates that both drugs killed the OVCAR-3 cells. The difference between EPD and cisplatin was that after EPD inoculation the mice looked very healthy while mice treated with cisplatin got very sick and had to be euthanised after 4 weeks of cisplatin treatment. Nonetheless, cisplatin proved very effective as a cytotoxic drug.

Ascites from several control mice were gathered and frozen down when the abdominal swelling was too much of a burden for the animals. The amount of ascites gathered was 6-7 ml/mouse.

In order to evaluate the long term effect of the EPD treatment, and to determine whether the reduction in abdominal swelling was permanent, three of the five mice that were treated with EPD for 6 weeks were kept alive for another month, without any further treatment. In one mouse the ascites returned, two mice did not develop ascites again. This could not be tested for cisplatin since all cisplatin-treated mice had to be euthanized after 4 weeks of treatment.

The compound EPD is a sesquiterpene lactone and its cytotoxicity has been shown in both in vitro and in vivo experiments. More important, mice injected twice a week for 6 weeks showed remission of cancer upon treatment. More importantly, and in contrast to mice injected with cisplatin, the mice injected with EPD looked very healthy, did not show any signs of side effects and all the animals survived the study.

Discussion

Two major sesquiterpenes of the eremophilanolide structure sub-type were identified by 1H-NMR and 13C-NMR experiments and by mass spectrometry and comparison with the published 1H-NMR (partial spectra) as eremophila-1(10)-11(13)-dien-12,8β-olide (EPD) and eremophila-1(10), 11(13)-dien-12-oic acid (EPA).

EPD, the most potent compound found in *C. amaranthoides*, was first described by Tanaka et al., 1976 (Chem. Pharm. Bull. 24(6): 1419-1421, 1976). They had isolated the compound from the root of *Xanthium canadense* Mill, (family Compositae).

In 1972 a diasterioisomer of EPD, (3aβ,4aα,5α,9aβ)-3a,4, 4a,5,6,7,9,9a-octahydro 4a,5-dimethyl-3-methylene naphtho [2,3-b]furan-2(3H)-2-one, was described as "napthofuranone" by the National Cancer Institute (NCI) in their "in vivo" anti-tumor screening data, testing the drug against P388 Leukemia in CD2F1 mice (NCI In Vivo Antitumor Screening Data. Cancer Chemotherapy Reports Vol. 3, No 2, 1972), but with no clear results. Also Bohlman and Zdero described a new SL with a structure as diastereoisomer of EPD (Chem. Ber. 109, 2651-2652, 1976.), but the structure has been disputed by Zoretic et al. in 1982 (J. Org. Chem 47:1327-1329, 1982).

An allergenic sesquiterpenelactone, alantolactone, found in "Elfdock" *Inula helenium* has been shown to be toxic to leukocytes. Although with the same weight and molecular formula as EPD it belongs to the eudesmanolide structure sub-type (Dupuis & Brisson. Chem. Biol. Interactions 15: 205-217, 1976.). This SL has a different chemical structure with different positions of one methyl and one double bond.

For biological activity even a difference of stereoisomers often results in large differences in potency and specificity.

EPA (Phytochemistry 16: 1302-1303, 1977), the other sesquiterpene found in C. amaranthoides in HPLC fractions 2 and 3, did not show cytotoxic effects on the cells tested. This is surprising since the structure of EPA is quite close to that of EPD, which shows very clear cytotoxic effects on cancer cells.

Besides the cytotoxic effects of the crude extracts of C. amaranthoides with clear effects at 10 μg/mL, the isolation of the biologically active compound EPD has been shown to kill completely ovarian cancer cells at lower concentrations than 10 μg/ml, such as 5 μg/mL but not at 1 μg/mL, although great cell loss was already seen. Interestingly, the crude plant extract had no effect on normal cells in vitro (fibroblasts, lymphocytes, the ovarian cells) at a concentration of 10 μg/mL; with EPD cancer cells were killed at 5 μg/mL while normal cells at that concentration were little affected.

Sesquiterpene lactones are known to be irritating to nose, eyes and gastrointestinal tract, while cattle sheep and horses are commonly exposed to poisoning "spewing sickness" but C. amaranthoides is liked by native animals (kangaroos) of Australia. There are no literature records about kangaroos and ovarian cancer.

Several experiments were performed to measure apoptosis using the Nicoletti assay (J Immunol. Methods 139: 271-279, 1991). After drug treatment with various concentrations of crude plant extract (1-50 μg/mL), the ovarian cancer cells were killed while normal cells such as skin fibroblasts were hardly affected.

Ovarian cancer has a poor prognosis. With more than 60% of the patients presenting the disease in stage III or IV, the tumor spread beyond the ovaries, combination chemotherapy with platinum and taxol after cytoreductive surgery give the most tolerated standard regimen (Markman. Hematol Oncol Clin N Am 17: 957-968, 2003; Bookman Met al. Int J Gynecol Cancer 13 (Suppl. 2); 149-155, 2003). The crude extract of C. amaranthoides has been compared with cisplatin and docetaxol, on both cancer- and normal cells. The crude extract was comparable with cisplatin on cancer cells (they were all killed), but normal cells were alive with 10 μg/mL with the crude extract of C. amaranthoides while both other drugs completely killed normal cells.

In vivo pilot experiments have been performed as described above and point to a clear and surprising effect of EPD over EPA: EPD emerges as a new potential anti-cancer drug for ovarian cancer (and other cancers) and may be used alone as sole active agent in a pharmaceutical composition or may be administered in combination with other anti-cancer agents.

The invention claimed is:

1. A method for the treatment of cancer, comprising administering to a subject in need thereof a therapeutically effective amount of a pharmaceutical composition comprising xanthanodien, or a pharmaceutically acceptable salt thereof, and a pharmaceutically acceptable carrier, wherein said cancer is selected from the group consisting of ovarian cancer, melanoma, sarcoma, colon cancer, thyroid cancer, leukemia and breast cancer.

2. The method of claim 1, wherein said therapeutically effective amount is about 0.0001 mg to about 1000 mg per kg body weight of said subject per 24 hours.

3. The method of claim 1 wherein said cancer is ovarian cancer.

4. The method of claim 1 wherein said cancer is melanoma.

5. The method of claim 1 wherein said method comprises a combination treatment regimen wherein the administering to a subject in need thereof of a therapeutically effective amount of a pharmaceutical composition comprising xanthanodien, or a pharmaceutically acceptable salt thereof, and a pharmaceutically acceptable carrier is used in conjunction with radiotherapy, chemotherapy, surgery, or other forms of medical intervention.

6. The method of claim 5, wherein said chemotherapy comprises the co-administration of xanthanodien and a chemotherapeutic or other anti-cancer agent selected from taxol, fluorouracil, cisplatin, oxaliplatin, α-interferon, vincristine, vinblastine, angioinhibins, doxorubicin, bleomycin, mitomycin C, phenoxodiol, methramycin, TNP-470, pentosan polysulfate, tamoxifen, LM-609, CM-101 and/or SU-101.

7. The method according to claim 6, wherein said coadministration of xanthanodien and said chemotherapeutic or other anti-cancer agent is simultaneous or sequential.

* * * * *